US00PP36944P2

(12) United States Plant Patent
Flore

(10) Patent No.: US PP36,944 P2
(45) Date of Patent: Sep. 9, 2025

(54) ***PHALAENOPSIS* PLANT NAMED 'MI02673'**

(50) Latin Name: *Phalaenopsis hybrida*
Varietal Denomination: MI02673

(71) Applicant: MICROFLOR N.V., Lochristi (BE)

(72) Inventor: Febe Flore, Lochristi (BE)

(73) Assignee: MICROFLOR N.V., Lochristi (BE)

( * ) Notice: Subject to any disclaimer, the term of this patent is extended or adjusted under 35 U.S.C. 154(b) by 0 days.

(21) Appl. No.: 19/096,409

(22) Filed: Mar. 31, 2025

Related U.S. Application Data

(60) Provisional application No. 63/572,673, filed on Apr. 1, 2024.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

(56) References Cited

U.S. PATENT DOCUMENTS

PP33,860 P2 * 1/2022 Van Swieten ..... A01H 6/62
Plt./311

* cited by examiner

*Primary Examiner* — Karen M Redden
(74) *Attorney, Agent, or Firm* — C. Anne Whealy

(57) ABSTRACT

A new and distinct cultivar of *Phalaenopsis* plant named 'MI02673', characterized by its upright plant habit; semi-erect to horizontally-orientated leaves; strong flowering stems; freely flowering habit; light purple to dark pink-colored flowers; and excellent postproduction longevity.

2 Drawing Sheets

Figure 1:
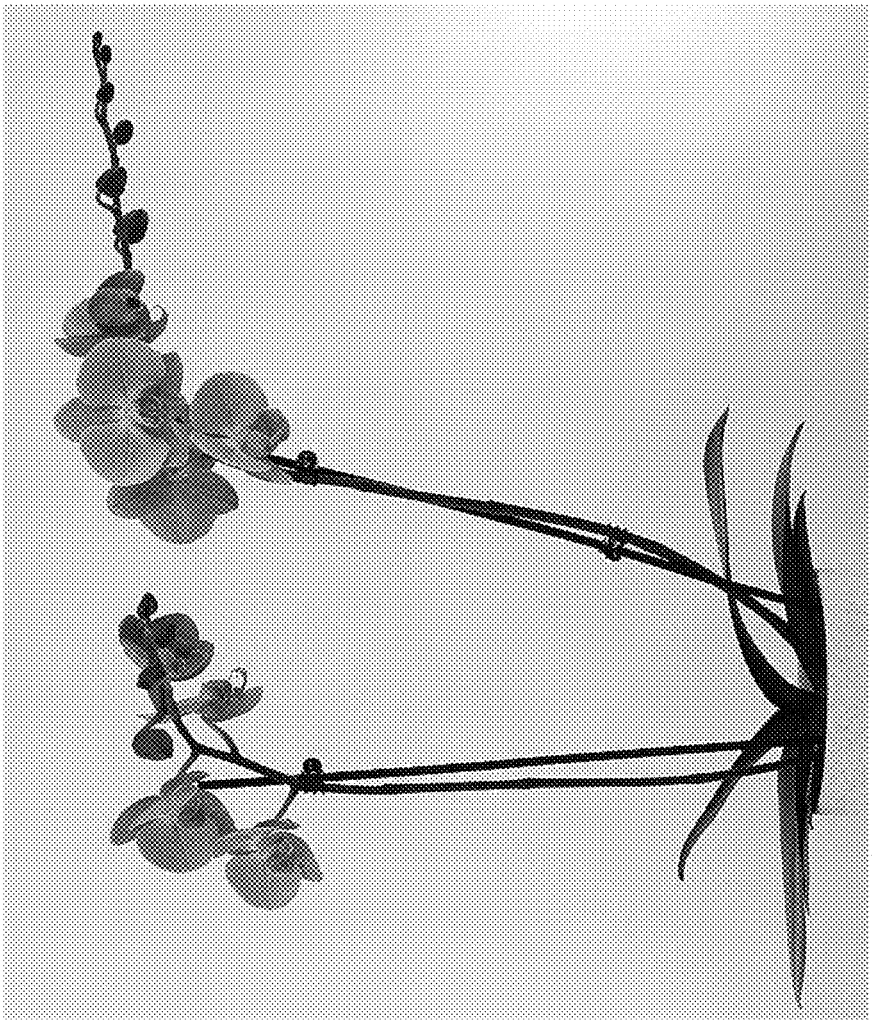

Botanical designation: *Phalaenopsis hybrida.*
Cultivar denomination: 'MI02673'.

REFERENCED TO CLOSELY-RELATED APPLICATIONS

A European Community Plant Breeder's Rights application for the instant plant was filed by the Applicant/Assignee, Microflor N.V. of Lochristi, Belgium on Mar. 25, 2025, application number A202501359. Foreign priority is not claimed to this application.

BACKGROUND OF THE INVENTION

The present invention relates to a new and distinct cultivar of *Phalaenopsis* plant, botanically known as *Phalaenopsis hybrida,* and hereinafter referred to by the name 'MI02673'.

The new *Phalaenopsis* plant is a product of a planned breeding program conducted by the Inventor in Lochristi, Belgium. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in May 2016 in Lochristi, Belgium of a proprietary selection of *Phalaenopsis hybrida* identified as code number MI01434, not patented, as the female, or seed, parent with a proprietary selection of *Phalaenopsis hybrida* identified as code number MI00019, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in June 2019.

Asexual reproduction of the new *Phalaenopsis* plant by in vitro meristem propagation in a controlled environment in Lochristi, Belgium since June 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI02673'. These characteristics in combination distinguish 'MI02673' as a new and distinct *Phalaenopsis* plant:

1. Upright plant habit.
2. Semi-erect to horizontally-orientated leaves.
3. Strong flowering stems.
4. Freely flowering habit with typically about two inflorescences per plant, each inflorescence with numerous flowers.
5. Light purple to dark pink-colored flowers.
6. Excellent postproduction longevity.

Plants of the new *Phalaenopsis* can be compared to plants of the female parent selection. Plants of the new *Phalaenopsis* differ primarily from plants of the female parent selection in the following characteristics:

1. Leaves of plants of the new *Phalaenopsis* are elliptic in shape whereas leaves of plants of the female parent selection are lanceolate in shape.

2. Plants of the new *Phalaenopsis* have larger flowers than plants of the female parent selection.
3. Petals and sepals of flowers of plants of the new *Phalaenopsis* are darker in color than petals and sepals of flowers of plants of the female parent selection.

Plants of the new *Phalaenopsis* can be compared to plants of the male parent selection. Plants of the new *Phalaenopsis* differ primarily from plants of the male parent selection in the following characteristics:

1. Leaves of plants of the new *Phalaenopsis* are elliptic in shape whereas leaves of plants of the male parent selection are narrowly obovate in shape.
2. Leaf apices of plants of the new *Phalaenopsis* are obtuse to unequal obtuse whereas leaf apices of plants of the male parent selection are more acute.
3. Petals and sepals of flowers of plants of the new *Phalaenopsis* are darker in color than petals and sepals of flowers of plants of the male parent selection.

Plants of the new *Phalaenopsis* can be compared to plants of *Phalaenopsis hybrida* 'PH00781', not patented. In side-by-side comparisons, plants of the new *Phalaenopsis* differ primarily from plants of 'PH00781' in the following characteristics:

1. Leaves of plants of the new *Phalaenopsis* are elliptic in shape whereas leaves of plants of 'PH00781' are narrowly obovate in shape.
2. Leaf apices of plants of the new *Phalaenopsis* are obtuse to unequal obtuse whereas leaf apices of plants of 'PH00781' are more acute.
3. Petals and sepals of flowers of plants of the new *Phalaenopsis* are darker in color than petals and sepals of flowers of plants of 'PH00781'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'MI02673' grown in a container.

Figure 2:
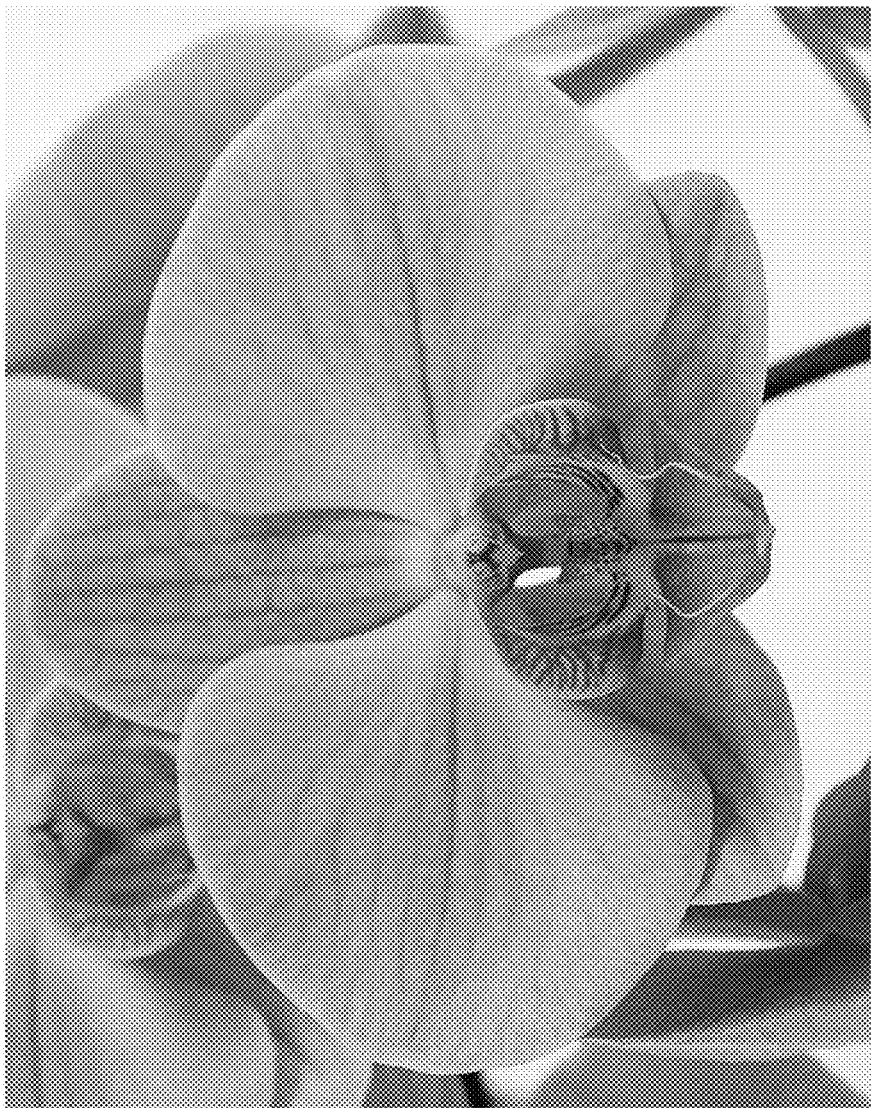

The photograph on the second sheet (FIG. 2) is a close-up view of typical flowers of 'MI02673'.

DETAILED BOTANICAL DESCRIPTION

The aforementioned photographs and following observations and measurements describe plants grown during the early autumn in 12-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/m$^2$ to 375 Watt/m$^2$. Plants were 72 weeks old when the photographs and the detailed description were taken. In the following description, color references are made to The Royal Horticultural Society Colour Chart, 2001 Edition, except where general terms of ordinary dictionary significance are used.

Botanical classification: *Phalaenopsis hybrida* 'MI02673'.

Parentage:

*Female parent*.—Proprietary selection of *Phalaenopsis hybrida* identified as code number MI01434, not patented.

*Male parent*.—Proprietary selection of *Phalaenopsis hybrida* identified as code number MI00019, not patented.

Propagation:

*Type*.—By in vitro meristem propagation.

*Time to initiate roots, summer*.—About nine to ten weeks at temperatures about 26° C.

*Time to initiate roots, winter*.—About ten to eleven weeks at temperatures about 26° C.

*Time to produce a rooted young plant, summer*.—About 140 to 160days at temperatures about 26° C.

*Time to produce a rooted young plant, winter*.—About 150 to 180days at temperatures about 26° C.

*Root description*.—Thick, fleshy; typically grey green in color; actual color of the roots is dependent on substrate composition, water quality, fertilizer, substrate temperature and age of roots.

*Rooting habit*.—Small amount of branching; sparse.

Plant description:

*Plant form and growth habit*.—Herbaceous epiphyte; upright plant habit with typically two inflorescences per plant, each inflorescence with numerous flowers; monopodial; vigorous growth habit and moderate growth rate.

*Plant height, substrate level to top of foliar plane*.—About 12 cm.

*Plant height, substrate level to top of inflorescences*.—About 49 cm.

*Plant diameter or spread*.—About 45 cm.

Leaf description:

*Arrangement and quantity*.—Distichous, simple; sessile; about seven leaves per plant.

*Length*.—About 20 cm.

*Width*.—About 7.3 cm.

*Aspect*.—Semi-erect to horizontal.

*Shape*.—Elliptic.

*Apex*.—Obtuse to unequal obtuse.

*Base*.—Sheathing.

*Margin*.—Entire.

*Texture and luster, upper and lower surfaces*.—Smooth, glabrous; glossy.

*Venation pattern*.—Camptodromous.

*Color*.—When opening, upper surface: Close to 139A; towards the base and margins, close to 187A. When opening, lower surface: Close to 187A. Fully expanded leaves, upper surface: Close to 137B; venation, close to 137B. Fully expanded leaves, lower surface: Close to 138B; venation, close to 138B.

Inflorescence description:

*Appearance and flowering habit*.—Showy zygomorphic flowers arranged on axillary branched racemes; typically two inflorescences per plant; each inflorescence with about ten to twelve flowers; flowers face outwardly on arching inflorescences supported by upright peduncles; flowers with three petals, two lateral petals and one center petal transformed into a labellum and three sepals.

*Fragrance*.—To date, none detected.

*Time to flower*.—Plants begin flowering about 16 weeks after an eight-week inductive cooling period; flowers open about five weeks after flower buds develop.

*Flower longevity*.—Long flowering period and excellent postproduction longevity, individual flowers maintain good substance for about nine weeks on the plant; flowers not persistent.

*Inflorescence length* (*lowermost flower to inflorescence apex*).—About 26 cm.

*Inflorescence width*.—Axially, about 49 cm and radially, about 30 cm.

*Flower buds*.—Height: About 2.2 cm. Diameter: About 2 cm. Shape: Ovate. Color: Close to 59A.

*Flower diameter*.—About 9.1 cm.

*Flower depth*.—About 2.9 cm.

*Petals, quantity and arrangement*.—Three, two lateral petals and one center petal transformed into a labellum; petals free and not imbricate.

*Lateral petals*.—Length: About 4.6 cm. Width: About 5.1 cm. Shape: Roughly flabellate. Apex: Rounded. Margin: Entire. Texture and luster, upper and lower surfaces: Smooth, glabrous, velvety; matte. Color: When opening, upper surface: Close to 80B; venation, close to 80A. When opening, lower surface: Close to 80C; venation, close to 80B. Fully opened, upper and lower surfaces: Close to 80C; venation, close to 80B; ground color becoming closer to 80B to 80C with subsequent development.

*Labella*.—Appearance: Tri-lobed with two lateral lobes and a central lobe. Central lobe length: About 2 cm. Central lobe width: About 2.1 cm. Shape, lateral lobes: Oblanceolate; apices, obtuse; and margins, entire. Shape, central lobe: Trullate; apices, cleft with short and narrow recurved cirrhose tips; margins, entire. Texture and luster, upper and lower surfaces: Smooth, glabrous, moderately velvety; matte. Callosities: Located at the base of the labellum and attachment point of the lateral petals; about 5 mm in length, about 6 mm in width and about 5 mm in height. Color, central lobe: When opening and fully opened, upper surface: Close to 80B; towards the base, close to 6A. When opening and fully opened, lower surface: Close to 80B. Color, lateral lobes: When opening and fully opened, upper surface: Close to 80A; towards the base, close to 155D with stripes, close to 46C; lower marginal edges, close to 6A. When opening and fully opened, lower surface: Close to 155C; towards the margins, close to 78D. Color, callosities: Close to 80A with fine stripes, close to 46C.

*Sepals*.—Quantity and arrangement: Three, two lower lateral sepals and one upper dorsal sepal. Length, lateral sepal: About 4 cm. Width, lateral sepals: About 2.8 cm. Length, dorsal sepal: About 4.3 cm. Width, dorsal sepal: About 3 cm. Shape, lateral sepals: Ovate. Shape, dorsal sepal: Elliptical. Apex, lateral sepals: Bluntly acute. Apex, dorsal sepal: Bluntly emarginate. Base, lateral and dorsal sepals: Acute to obtuse. Margin, lateral and dorsal sepals: Entire. Texture and luster, lateral and dorsal sepals, upper and lower surfaces: Smooth, glabrous, velvety; matte. Color, lateral and dorsal sepals: When opening, upper surface: Close to 80C; venation, close to 80B. When opening, lower surface: Close to 72B; venation, close to 72A. Fully opened, upper surface: Close to 80D; venation, close to 80C; color does not change with subsequent development. Fully opened, lower surface: Close to 80B; venation, close to 80A; color does not change with subsequent development.

*Peduncles*.—Length: About 62 cm. Diameter, proximally: About 6 mm. Strength: Strong, somewhat flexible. Aspect: Mostly upright. Texture and luster: Smooth, glabrous; matte. Color: Close to 138A; dense and random dots, close to 200A.

*Pedicels*.—Length: About 4.1 cm. Diameter: About 4 mm. Strength: Moderately strong; flexible. Aspect: About 90° from peduncle axis. Texture and luster: Smooth, glabrous; matte. Color: Close to 146A; at the base and apex, close to 160D.

*Reproductive organs*.—Androecium: Column length: About 9 mm. Column width: About 7 mm. Column color: Close to 69D; central stripe, close to 78A. Pollinia quantity: Two. Pollinia diameter (per two pollinia): About 3 mm. Pollinia color: Close to 26A. Gynoecium: Stigma length: About 3 mm. Stigma width: About 3 mm. Stigma shape: Reniform. Stigma color: Close to 69D. Ovary length: About 1.4 cm. Ovary diameter: About 3 mm. Ovary color: Close to 160D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 40° C. and to be suitable for USDA Hardiness Zones 10 and higher.

It is claimed:

1. A new and distinct *Phalaenopsis* plant named 'MI02673' as herein illustrated and described.

* * * * *